US011004547B2

(12) United States Patent
Valdes et al.

(10) Patent No.: US 11,004,547 B2
(45) Date of Patent: May 11, 2021

(54) SYSTEMS AND METHODS OF AGGREGATING HEALTHCARE-RELATED DATA FROM MULTIPLE DATA CENTERS AND CORRESPONDING APPLICATIONS

(71) Applicant: b.well Connected Health, Inc., Eldersburg, MD (US)

(72) Inventors: Kristen Valdes, Eldersburg, MD (US); Philips Johnson, Elderburg, MD (US); Yelena Balin, Eldersburg, MD (US)

(73) Assignee: b.well Connected Health, Inc., Eldersburg, MD (US)

( * ) Notice: Subject to any disclaimer, the term of this patent is extended or adjusted under 35 U.S.C. 154(b) by 378 days.

(21) Appl. No.: 15/800,772

(22) Filed: Nov. 1, 2017

(65) Prior Publication Data

US 2018/0150599 A1    May 31, 2018

Related U.S. Application Data

(60) Provisional application No. 62/416,106, filed on Nov. 1, 2016.

(51) Int. Cl.
| | |
|---|---|
| *G16H 10/60* | (2018.01) |
| *G06F 16/904* | (2019.01) |
| *G06Q 40/08* | (2012.01) |
| *G16H 15/00* | (2018.01) |

(52) U.S. Cl.
CPC .......... *G16H 10/60* (2018.01); *G06F 16/904* (2019.01); *G06Q 40/08* (2013.01); *G16H 15/00* (2018.01)

(58) Field of Classification Search
CPC combination set(s) only.
See application file for complete search history.

(56) References Cited

U.S. PATENT DOCUMENTS

| | | | |
|---|---|---|---|
| 9,454,577 B1* | 10/2010 | Kapoor et al. | |
| 10,468,126 B1* | 8/2015 | Harding et al. | |
| 2003/0195771 A1* | 10/2003 | Fitzgerald et al. | |
| 2004/0186746 A1* | 9/2004 | Angst et al. | |
| 2012/0232929 A1* | 9/2012 | Experton | |
| 2014/0278449 A1* | 9/2014 | Kharraz Tavakol | |
| 2014/0310683 A1* | 10/2014 | McCarty et al. | |
| 2015/0154528 A1* | 6/2015 | Kharraz Tavakol | |
| 2015/0187036 A1* | 7/2015 | Wang et al. | |
| 2016/0063189 A1* | 3/2016 | Soon-Shiong et al. | |
| 2016/0132645 A1* | 5/2016 | Charpentier et al. | |
| 2016/0292456 A1 | 10/2016 | Dubey et al. | |
| 2017/0006135 A1* | 1/2017 | Siebel et al. | |
| 2017/0161452 A1* | 6/2017 | Bain | |
| 2017/0169173 A1* | 6/2017 | Snow, Jr. et al. | |
| 2017/0300634 A1* | 10/2017 | Chiang et al. | |
| 2019/0279135 A1* | 9/2019 | Wilkerson et al. | |

FOREIGN PATENT DOCUMENTS

WO        2016077792 A1    5/2016

* cited by examiner

*Primary Examiner* — Michael Tomaszewski
*Assistant Examiner* — William T. Monticello
(74) *Attorney, Agent, or Firm* — Ramya Possett

(57) ABSTRACT

Described herein are systems and methods for receiving healthcare data from a plurality data sources that generate and store data in various data model regimes, many of which are not standardized or are variants of a standard. The stored data may then be used to provide a plurality of customized execution environments and graphical user interfaces (GUIs) to users, based on each user's electronic healthcare records, insurance records, and wearable device data.

20 Claims, 12 Drawing Sheets

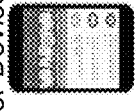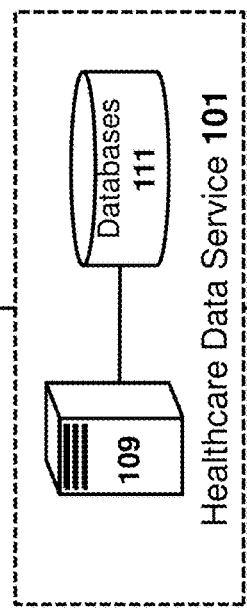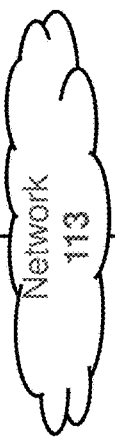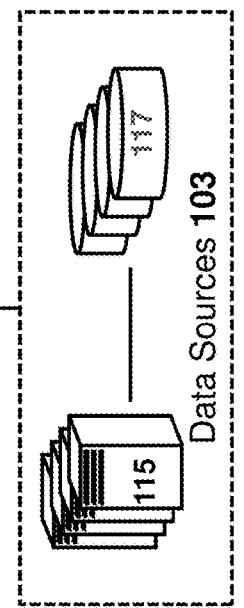
FIG. 1A

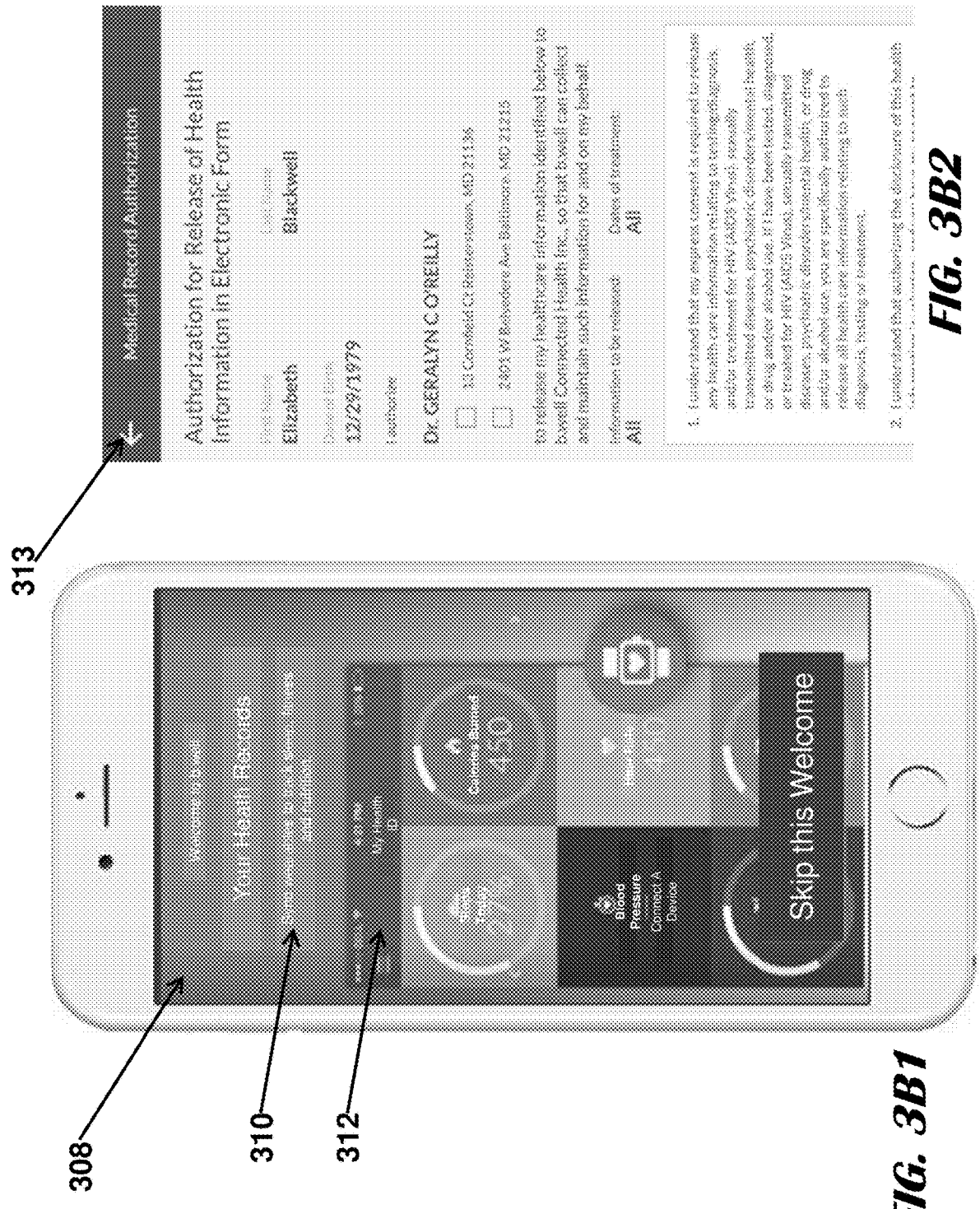
FIG. 3B2
FIG. 3B1

SYSTEMS AND METHODS OF AGGREGATING HEALTHCARE-RELATED DATA FROM MULTIPLE DATA CENTERS AND CORRESPONDING APPLICATIONS

CROSS-REFERENCE TO RELATED APPLICATIONS

This application claims priority to U.S. Provisional Patent Application Ser. No. 62/416,106, filed on Nov. 1, 2016, which is hereby incorporated by reference in its entirety.

TECHNICAL FIELD

This application relates generally to healthcare-related software applications and enterprise data management.

BACKGROUND

Electronic healthcare records (EHR) are generated and stored according to various company-specific, product-specific, or standardized data models, such as HL7 and FHIR. But healthcare software applications may use variants of standard data models or customized data models that are not openly available. Moreover, EHR health data is often fragmented, but still growing more so by the day. Consequently, stakeholders (e.g., patients, insurers, care providers, employers) do not have access to comprehensive datasets that needed to control health outcomes, and consumers historically have not had any access to their own health data. Additionally, as user devices and products moving into a digital age where consumers can access fitness, nutrition, diagnosis and have medical encounters all online through a growing number of platforms and providers, there is a growing need for data to be aggregated and standardized across disparate data sources.

SUMMARY

Disclosed herein are systems and methods capable of addressing the above-described shortcomings and may also provide any number of additional or alternative benefits and advantages. As described herein, embodiments of the present disclosure relate to systems, apparatuses, methods, and computer program products for receiving healthcare data from a plurality data sources that generate and store data in various data model regimes, many of which are not standardized or are variants of a standard. The stored data may then be used to provide a plurality of customized execution environments and graphical user interfaces (GUIs) to users, based on each user's electronic healthcare records, insurance records, and wearable device data.

Disclosed herein are systems, apparatuses, methods, and computer program products for healthcare related software applications and enterprise data management by collecting healthcare data records and healthcare activity for a user to provide the user with healthcare reports and insights created by consolidating all healthcare records and activity into a single healthcare record generated by a common data model and then analyzing the single healthcare record. Such systems, apparatuses, and methods of the present disclosure maximize healthcare risk prevention by using risk driven algorithms that learns from evolving continuous healthcare trends of the user, increases speed of the healthcare risk detection by dynamically re-evaluating risk as new healthcare information becomes available for the user, and provides scalable healthcare solution to the user to serve detected healthcare problem.

Systems, apparatuses, and methods of the present disclosure execute a computer processor or any other server of a healthcare data system that performs various processes to collect data from multiple healthcare data-generating systems containing various data fields and data types, indicating healthcare related information of users, in order to determine whether the healthcare information contain attributes matching attributes of one or more scenarios. Using the healthcare information, the computer processor or any other server of the healthcare data system generate healthcare profiles that are associated with users of the healthcare data system and determine any data gaps in the healthcare profiles, which the computer or any other server of the healthcare data system eliminates by collecting additional and necessary data before processing to data analysis of the healthcare profiles. Analyst computers may query and fetch these updated and completed healthcare profiles from a database, and then generate and present healthcare reports and insights on a dashboard of a user computing device. This can ensure that the user is provided with accurate healthcare information on the dashboard of the user computing device all the time to maximize healthcare risk prevention.

In one embodiment, a computer-implemented method may include receiving, by a computer, a set of one or more healthcare data records containing a user identifier from one or more healthcare data-generating systems configured to generate a corresponding healthcare data record, wherein the one or more healthcare data-generating systems are configured to generate the corresponding healthcare data record according to one or more data models associated with one or more formats and one or more data types. The computer-implemented method may further include standardizing, by the computer, the set of one or more healthcare data records received from the one or more healthcare data-generating systems according to a common data model comprising mappings specifying transformations from the one or more formats for all healthcare data records having all of the one or more data types to a single format and single data type. The computer-implemented method may further include storing, by the computer, the standardized set of one or more healthcare data records into a first database configured to store a plurality of healthcare data records associated with a plurality of user identifiers. The computer-implemented method may further include generating, by the computer, in a second database, a user healthcare profile of a user associated with the user identifier, the user healthcare profile comprising one or more data fields containing data from the standardized set of one or more healthcare data records associated with the user identifier in the first database, wherein the second database is configured to store a plurality of user healthcare profiles associated with a plurality of user identifiers. The computer-implemented method may further include determining, by the computer, one or more action items associated with the data in each of the one or more data fields in the user healthcare profile, wherein each action item is programmed to be performed within a predetermined period of time. The computer-implemented method may further include determining, by the computer, whether a record of execution of the one or more action items is available from the one or more healthcare data-generating systems after the predetermined period of time elapses, wherein the computer is configured to trigger a monitoring window for a time period from determination of the one or more action items until the predetermined period of time elapses. The computer-implemented method may further include identifying, by the computer, one or more data gaps corresponding to missing data in the user healthcare profile based on examination of data in the one or more data fields of the user healthcare profile that determines a link between data records contained in each of the one or more data fields, wherein the examination further comprises determining by the computer whether there is no record of execution of the one or more action items within the predetermined period of time. The computer-implemented method may further include upon the computer identifying the one or more data gaps in the user healthcare profile when there is no link between the data records contained in each of the one or more data fields and there is no record of execution of the one or more action items within the predetermined period of time: transmitting, by the computer, a web link to a secure webpage comprising a request to a user computing device operated by the user, wherein the request comprises an instruction to populate missing information in the one or more data gaps in the user healthcare profile and execute the one or more action items; updating, by the computer, the user healthcare profile in the second database upon receiving the information corresponding to the one or more data gaps from the user computing device; and displaying, by the computer, one or more healthcare reports based on evaluation of the data in the one or more data fields of the user healthcare profile on a graphical user interface of the user computing device.

In another embodiment, a system may include a first database configured to store healthcare data records and a second database configured to store user healthcare profiles. The system may further include a computer. The computer may be configured to a set of one or more healthcare data records containing a user identifier from one or more healthcare data-generating systems configured to generate a corresponding healthcare data record, wherein the one or more healthcare data-generating systems are configured to generate the corresponding healthcare data record according to one or more data models associated with one or more formats and one or more data types. The computer may be configured to standardize the set of one or more healthcare data records received from the one or more healthcare data-generating systems according to a common data model comprising mappings specifying transformations from the one or more formats for all healthcare data records having all of the one or more data types to a single format and single data type. The computer may be configured to store the standardized set of one or more healthcare data records into a first database configured to store a plurality of healthcare data records associated with a plurality of user identifiers. The computer may be configured to generate, in a second database, a user healthcare profile of a user associated with the user identifier, the user healthcare profile comprising one or more data fields containing data from the standardized set of one or more healthcare data records associated with the user identifier in the first database, wherein the second database is configured to store a plurality of user healthcare profiles associated with a plurality of user identifiers. The computer may be configured to determine one or more action items associated with the data in each of the one or more data fields in the user healthcare profile, wherein each action item is programmed to be performed within a predetermined period of time. The computer may be configured to determine whether a record of execution of the one or more action items is available from the one or more healthcare data-generating systems after the predetermined period of time elapses, wherein the computer is configured to trigger a monitoring window for a time period from determination of the one or more action items until the predetermined period of time elapses. The computer may be configured to identify one or more data gaps corresponding to missing data in the user healthcare profile based on examination of data in the one or more data fields of the user healthcare profile that determines a link between data records contained in each of the one or more data fields, wherein the examination further comprises determining by the computer whether there is no record of execution of the one or more action items within the predetermined period of time. The computer may be configured to, upon the computer identifying the one or more data gaps in the user healthcare profile when there is no link between the data records contained in each of the one or more data fields and there is no record of execution of the one or more action items within the predetermined period of time: transmit a web link to a secure webpage comprising a request to a user computing device operated by the user, wherein the request comprises an instruction to populate missing information in the one or more data gaps in the user healthcare profile and execute the one or more action items; update the user healthcare profile in the second database upon receiving the information corresponding to the one or more data gaps from the user computing device; and display one or more healthcare reports based on evaluation of the data in the one or more data fields of the user healthcare profile on a graphical user interface of the user computing device.

In another embodiment, a computer-implemented method may include receiving, by a computer, a set of one or more healthcare data records containing a user identifier from one or more healthcare data-generating systems configured to generate a corresponding healthcare data record, wherein the one or more healthcare data-generating systems are configured to generate the corresponding healthcare data record according to one or more data models associated with one or more formats and one or more data types. The computer-implemented method may further include standardizing, by the computer, the set of one or more healthcare data records received from the one or more healthcare data-generating systems according to a common data model comprising mappings specifying transformations from the one or more formats for all healthcare data records having all of the one or more data types to a single format and single data type. The computer-implemented method may further include storing, by the computer, the standardized set of one or more healthcare data records into a first database configured to store a plurality of healthcare data records associated with a plurality of user identifiers. The computer-implemented method may further include generating, by the computer, in a second database, a user healthcare profile associated with the user identifier, the user healthcare profile comprising one or more data fields containing data from the standardized set of one or more healthcare data records associated with the user identifier in the first database, wherein the second database is configured to store a plurality of user healthcare profiles associated with a plurality of user identifiers. The computer-implemented method may further include identifying, by the computer, one or more data gaps corresponding to missing data in the user healthcare profile associated with a user based on examination of data in the one or more data fields of the user healthcare profile, wherein the examination comprises determining by the computer a link between data records contained in each of the one or more data fields. The computer-implemented method may further include upon the computer identifying the one or more data gaps in the user healthcare profile associated with the user when there is no link between the data records contained in each of the one or more data fields: transmitting, by the computer, a web link to a secure webpage comprising a request to populate missing information in the one or more data gaps in the user healthcare profile to a user computing device operated by the user; updating, by the computer, the user healthcare profile in the second database upon receiving the information corresponding to the one or more data gaps from the user computing device; and displaying, by the computer, one or more healthcare reports based on evaluation of the data in the one or more data fields of the user healthcare profile on a graphical user interface of the user computing device.

In another embodiment, a system may include a first database configured to store healthcare data records and a second database configured to store user healthcare profiles. The system may further include a computer. The computer may be configured to receive a set of one or more healthcare data records containing a user identifier from one or more healthcare data-generating systems configured to generate a corresponding healthcare data record, wherein the one or more healthcare data-generating systems are configured to generate the corresponding healthcare data record according to one or more data models associated with one or more formats and one or more data types. The computer may be further configured to standardize the set of one or more healthcare data records received from the one or more healthcare data-generating systems according to a common data model comprising mappings specifying transformations from the one or more formats for all healthcare data records having all of the one or more data types to a single format and single data type. The computer may be further configured to store the standardized set of one or more healthcare data records into the first database configured to store a plurality of healthcare data records associated with a plurality of user identifiers. The computer may be further configured to generate in the second database a user healthcare profile associated with the user identifier, the user healthcare profile comprising one or more data fields containing data from the standardized set of one or more healthcare data records associated with the user identifier in the first database, wherein the second database is configured to store a plurality of user healthcare profiles associated with a plurality of user identifiers. The computer may be further configured to identify one or more data gaps corresponding to missing data in the user healthcare profile associated with a user based on examination of data in the one or more data fields of the user healthcare profile, wherein the examination comprises determining by the computer a link between user actions and sources of data contained in the one or more data fields. The computer may be further configured to upon the computer identifying the one or more data gaps in the user healthcare profile associated with the user: transmit a web link to a secure webpage comprising a request to populate missing information in the one or more data gaps in the user healthcare profile to a user computing device operated by the user; update the user healthcare profile in the second database upon receiving the information corresponding to the one or more data gaps from the user computing device; and display one or more healthcare reports based on evaluation of the data in the one or more data fields of the user healthcare profile on a graphical user interface of the user computing device.

It is to be understood that both the foregoing general description and the following detailed description are exemplary and explanatory and are intended to provide further explanation of the invention as claimed.

BRIEF DESCRIPTION OF THE DRAWINGS

The accompanying drawings constitute a part of this specification and illustrate an embodiment of the invention and together with the specification, explain the invention.

FIG. 1A shows components of an exemplary healthcare data system, according to an exemplary embodiment.

FIG. 3B1 illustrates a graphical user interface showing a webpage executed on a computing device of a user, according to an exemplary embodiment.

FIG. 3B2 illustrates a graphical user interface showing a webpage executed on a computing device of a user, according to an exemplary embodiment.

FIG. 3I illustrates a graphical user interface showing a webpage executed on a computing device of a user, according to an exemplary embodiment.

DETAILED DESCRIPTION

Figure 1B:
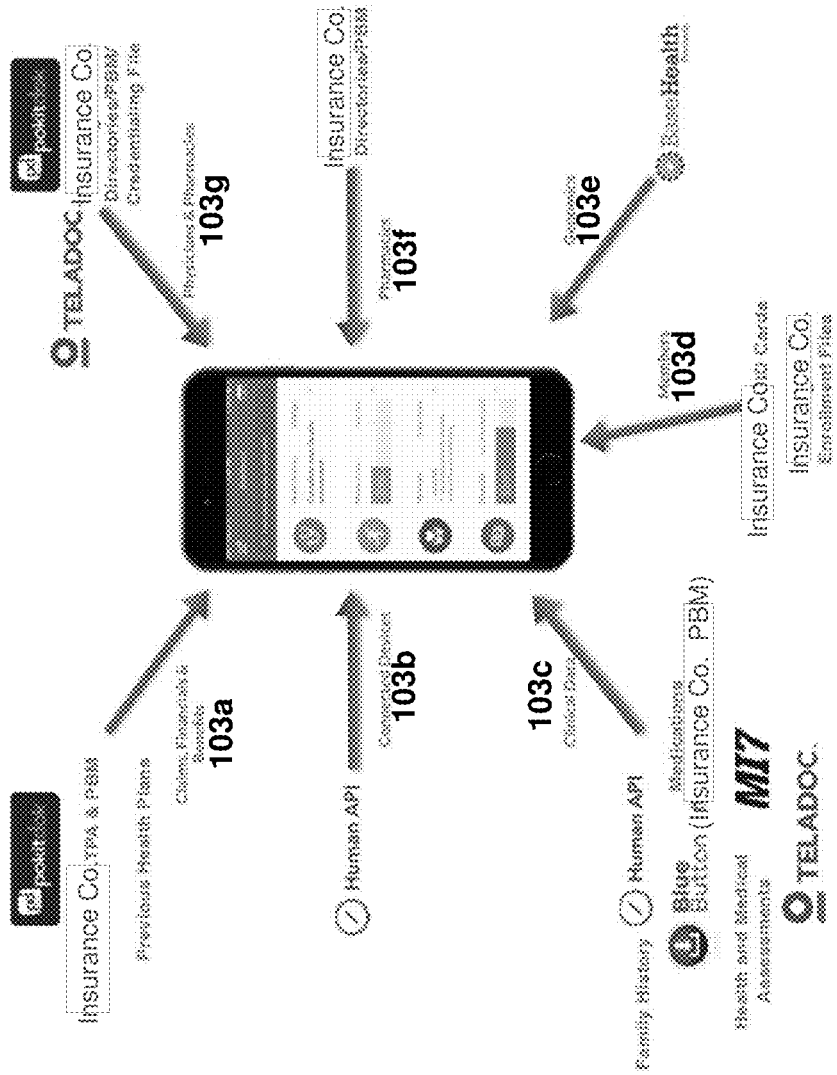
FIG. 1B shows exemplary data sources of a healthcare data system, according to an exemplary embodiment.

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

FIG. 1A shows components of an exemplary healthcare data system 100, which may include a health data service 101, one or more data sources 103, and user devices 107. The health data service 101, the data sources 103, and the user computing devices 107 are connected to each other through a network 113. The examples of the network 113 may include, but are not limited to, private or public LAN, WLAN, MAN, WAN, and the Internet. The network 113 may include both wired and wireless communications according to one or more standards and/or via one or more transport mediums. The communication over the network 113 may be performed in accordance with various communication protocols such as Transmission Control Protocol and Internet Protocol (TCP/IP), User Datagram Protocol (UDP), and IEEE communication protocols. In one example, the network 113 may include wireless communications according to Bluetooth specification sets, or another standard or proprietary wireless communication protocol. In another example, the network 113 may also include communications over a cellular network, including, e.g. a GSM (Global System for Mobile Communications), CDMA (Code Division Multiple Access), EDGE (Enhanced Data for Global Evolution) network. In some embodiments, all the communication between devices of the healthcare data system 100 may be performed over secure/HIPAA compliant protocols/mediums.

The health data service 101 may comprise a data server 109 and one or more service databases 111. The one or more service databases 111 may include a first database configured to store healthcare data records of users and a second database configured to store user healthcare profiles of the users. The first database may include one or more first sub-databases and each of the one or more first sub-databases may be configured to store the healthcare data records of users. The second database may include one or more second sub-databases and each of the one or more second sub-databases may be configured to store the user healthcare profiles of the users. In some embodiments, a single database may be configured to store the healthcare data records of users and the user healthcare profiles of the users. The health data server 101 may receive data records of various data types over one or more networks 113 from the data sources 103; each data source 103 may comprise a data source device 115 (for example, a healthcare data-generating system/device) and/or a source database 117. In operation, the data server 109 of the health data service 101 may receive data from a variety of data sources 103 over the one or more networks 113. The data server 109 may then standardize the received data according to a common data model, and store the standardized health data into a service database 111. The data server 109 may then execute one or more analytics processes on the standardized health data and provide the standardized health data over the one or more networks 113 to the user device 107 that may present health data reports and insights through various interactive graphical user interfaces (GUIs) to an end user, in accordance with the particular function or application executed by the user computing device 107.

A health data service 101 may receive records from a variety of data sources 103, and may convert the arriving data into a standardized data model that may be used to generate various GUIs or used to generate certain analytical data values resulting from various analytical algorithm models executed by a data server 109. In some embodiments, the health data service 101 may generate and transmit a request to a user on a user device 107 to receive records, and then the user may provide the health data service 101 access to the data sources 103 for obtaining the records. In some embodiments, the health data service 101 may generate and transmit a request to a user on a user device 107 to receive records, and then the user may access the data sources 103 for obtaining the records, and then transmit the records to the health data service 101. The records regarding the individual user/patient may be received and/or collected from diverse data sources 103 (as depicted in FIG. 1B) including, but not limited to information from claims through previous health plans 103a, connected devices 103b, clinical data 103c, member data 103d, genomics data 103e, pharmacy data 103f, physician data 103g, and other sources such as multiple EMR's being used from different providers providing care to that user/patient, medication records from the pharmacy benefit managers ("PBMs"), information from labs and imaging centers, and direct input by the user/patient to provide a unified personal/individual health record.

In some embodiments, the data collected from the diverse data sources 103 is organized into an individual health record for the user/patient. For instance, the data server 109 may generate user healthcare profile records for the users that is compiled using the incoming data records received from the various data sources 103 such as user/patient questionnaires or direct input, medical devices, patient portals, EMR systems, claims files, health plans, pharmacy benefits managers, labs, imaging centers, freestanding outpatient facilities, hospitals, physicians, and wearable devices. In some embodiments, the data server 109 may receive data records from the various data sources 103 and then convert the inbound data from a source data model, of the data source 103, to a standardized model employed by the various components of the healthcare data service 101. In order to convert the incoming data records, the data server 109 may execute one or more application programming interfaces (APIs) that map the data fields of the inbound data records to the data fields of the standardized model. For instance, records arriving from the data source 103 employing a healthcare application (e.g., AllScripts®) may provide inbound records having a first data model (e.g., HL7). These inbound records would then be converted by the data server 109 to the standardized model, associated with a consumer identifier (consumer ID) and stored into the service database 111. In one example, the individual healthcare data records collected from the variety of data sources 103 by the data server 109 may be integrated with universal health care concept codes of the standardized model to allow the healthcare data records to be encoded under specific medical diagnostic concepts. In some cases, the data server 109 may capture, share, and aggregate the healthcare data records collected from the variety of data sources 103 in a consistent manner by the standardized model universal health care concept codes terminology. The terminology may contain hierarchically specified health care concepts, each with unique meanings and logic-based definitions. Additionally, the health care concepts may have distinct relationships that support reliability and consistency for healthcare data record retrieval from the variety of data sources 103. As used herein, the universal health care concept codes corresponds to a standardized data model language that enables a consistent way of indexing, storing, retrieving, formatting, and aggregating healthcare data record across specialties and sites of medical care obtained from the variety of data sources 103. Each "universal health care concept code" is a unique identifier indicative of a node in a hierarchy of health care concepts to which other types of healthcare data record obtained from the variety of data sources 103 can be mapped.

A data server 109 may be any computing device comprising a processor and non-transitory machine-readable storage media storing software modules that instruct the processor to execute the various processes and tasks described herein. Non-limiting examples of the data server 109 may include a workstation computer, a server computer, a laptop, and a tablet device. For ease of explanation, FIG. 1 shows a single computing device functioning as the data server 109. However, it should be appreciated that some embodiments may comprise any number of the data servers 109 capable of performing the various tasks described herein.

The data server 109 may receive healthcare data records from various types of data sources 103. The healthcare data records may be log files or other machine-readable code containing various data fields describing detected user actions and sources of data associated with a user identifier. The data server 109 may generate a notification upon receiving healthcare data records from the data sources 103. The data fields of healthcare data records may contain data fields associated with the detected user actions and sources of data associated with the user identifier, such as data fields describing a source device in the data sources 103. Upon receiving the healthcare data records, the data server 109 or any other server of the system 100 may associate the healthcare data records with a user account based on the data fields of the healthcare data records associated with user identifier. The healthcare data records may, for example, contain a data field indicating a user identifier value that is unique to the user. The data server 109 may then store the healthcare data records into the database 111. Simultaneously or at some other time, the data server 109 may generate or update a user profile for the user identifier, which is a log file or any other machine-readable code containing data fields that are populated with data that is based on the healthcare data records associated with the same user identifier. Regardless of the number of healthcare data records received for the user identifier from the healthcare data-generating systems and the data sources 103, the database 111 contains only a single user profile for the particular user identifier.

In operation, the data server 109 may execute one or more software modules (e.g., APIs, web hooks, and web sprockets) configured to consume (e.g., retrieve/pull, receive), from various data sources 103, inbound data records that may then be parsed and reconstructed into the standardized data model format of the healthcare data service 101. The interface software modules may be configured to receive or pull data from particular data sources 103, as required by the particular data source 103. In some cases, a data source 103 may be configured to transmit a set of database records at regular interval, using a data transfer protocol (e.g. FTP, SFTP). Using inbound data records received from the various data sources 103, the software modules executed by the data server 109 may generate database records for the service database 111. Data models may define the data fields of inbound records and/or the data fields of the standardized data model, allowing the data server 109 to map incoming data models to the standardized data model of the healthcare data service 101. In some implementations, an inbound interface software module of the data server 109 may compare certain fields of two inbound data records arriving from disparate data sources 103, to determine whether the two inbound records are related to the same patient. The data server 109 may determine whether a new inbound record is related to the same patient of an existing record previously stored in a service database 111. The data server 109 may execute one or more analytics algorithms that may perform any number of analytics algorithms, such as cross-referencing data, and correlating data, and/or performing any number of metrics calculations, using data stored in the service databases 111.

As mentioned, the healthcare data service 101 may comprise one or more service databases 111 that may be hosted on one or more computing devices, such as server computers, workstation computers, laptops, mobile devices, and tablets. The service databases 111 may store data records comprising data fields that are associated with particular consumers or patients, groups of consumers, financial institutions (e.g., insurers), and healthcare providers. In some embodiments, the data server 109 may parse certain data fields of an inbound record into distinct records or fields of data records of the service database 111 in accordance with the standardized model, as indicated by the execution of the API. It should be appreciated that, although the exemplary system 100 shows only one service database 111, however the healthcare data service 101 may comprise any number of service databases 111, hosted on any number computing devices, which may be any computing device comprising a non-transitory machine-readable storage medium and capable of performing the various tasks described herein.

The data server 109 may be coupled to the data sources 103 via one or more internal or external networks 113. The data server 109 may execute various processes on incoming healthcare data records received from the data sources 103, such as data field formatting or identifying an associated user and then generating the user profile/record. Each user profile/record corresponds to a form such as a healthcare form or application such as a healthcare application, and contains various fields that are associated with instances of the form or application. The data server 109 initially populate user profile/record with information provided from the user, the one or more healthcare data-generating systems 115, other records in the data sources 103 or another source. After the user profile/record is initially populated, the data server 109 assigns status values to the fields in the user profile/record. The data server 109 may execute instructions to indicate a status of fields in the user profile/record stored in the database 111. In some cases, the data server 109 automatically assigns a status to each field in the user profile/record. To automatically assign status values to fields in the user profile/record, the data server 109 compares the data stored in each field to other data associated with the user. Referring to healthcare record context, for instance, certain fields in the user profile/record may be populated for every user including healthcare data collected from the data sources 103. In some cases, the format of the data provided in each field may be defined, for instance, weight field should include a kilograms. A set of rules reflecting the format may be obtained by the data server 109 from the database 111. The data server 109 in turn can automatically assign status values to fields in the user profile/record based on the rules, for instance, assigning a value of missing data to any field where data is expected and is not there, a status of incorrect data to any field where the data provided does not conform to an expected value, a status of incomplete data where data entered is only partial, or by any other status that could be predefined by the data server 109.

In some alternate embodiments, the data server 109 may execute a set of one or more scenario attribute models on the user profile/record to determine whether a data gap is present within the user profile/record. Scenario models may be computer files stored on the data server 109 or separate database device, such as the database 111, and comprise a set of attributes that indicate a type of potential data gap. Upon the execution of the scenario models, the data server 109 may identify data field entries in the user healthcare profiles to determine one or more matches to corresponding attributes in the scenario models. In one example, the data server 109 upon processing the incoming healthcare data records of the user may identify a data gap where the data server 109 may determine that the user got a referral from a primary care doctor to see an orthopedic doctor but the data server 109 did not identify any visit by the user to the orthopedics doctor on processing of the user healthcare data records. In such a case, the data server 109 may generate a flag for potential gap or missing information regarding potential orthopedics doctor visit by the user. In another example case, the data server 109 on processing the incoming healthcare data records of the user may identify a data gap where the user is taking a medication for a disease such as high blood pressure, but the data server 109 did not identify a doctor visit by the user where the user actually got diagnosed with high blood pressure on processing of the user healthcare data records. In such a case, the data server 109 may generate a flag for potential gap or missing information regarding potential doctor visit by the user. In yet another example case, the data server 109 upon processing two or more incoming healthcare data records of the user received over a period of time may identify a data gap where the data server 109 may determine a status of update in the user healthcare condition. For instance, the data server 109 may receive a healthcare data record (in a healthcare form) of a user every month, and then the data server 109 may compare the current healthcare data record in the current form with previous healthcare data in previous forms to determine a status update of the user healthcare condition user, that is, determining whether the user healthcare condition is becoming better, worse, or stagnant based on comparison of current healthcare data with previous healthcare data. In such a case, the data server 109 may generate a flag for potential gap regarding potential change in the healthcare condition of the user.

The data server 109 stores the potential gap or missing information in the database 111 and is used by the data server 109 to determine what follow up actions need to be taken. For instance, in some embodiments, the data server 109 may generate an alert upon identifying the potential gap or missing data in the healthcare data records. In some embodiments, the data server 109 may determine how to obtain the required data or generate requests for confirmations of the missing data from the user. In some embodiments, another server of a centrally hosted the system 100 receives a notification of status information from the data server 109 specifying relevant missing data fields and/or records, the status of the data fields, and how the missing information should be recovered. The notification may provide that several different data sources 103 need to be queried for missing information, for instance, different healthcare data-generating systems 115 or users, if the information resides in different places. The data server 109 issues requests to all the different sources of data, such as different healthcare data-generating systems 115, and thereby minimizing the hassle for the user to provide missing information.

In some embodiments, the data server 109 queries the different healthcare data-generating systems 115 and other data sources 103 on a regular basis or in response to indication of missing data, and retrieves information about missing records that require follow up action. In some cases, the data server 109 uses the status of the missing information to generate a request to be sent to a user computing device 107, based on instructions from the user, stored in the database 111. In some embodiments, the data server 109 solicits missing information electronically, through an email, chat, or other request. The request may be automatically formulated and sent by the data server 109 or may be created and provided to the user computing device 107 through an interface for verification before sending. The request may include a web link to a secure webpage or a data object that can be populated, saved, and returned to the data server 109. For example, the webpage contains the missing data fields and spaces to fill in the missing data. The webpage may be provided with options for communicating with the data server 109, for instance, including by sending an email message or initiating a chat. The webpage may further include various links to information about the requested data, and an option to provide a comment for any of the missing data fields. In some other instances, the request may solicit a response from a user computing device 107 in the form of a return email. In some other embodiments, the data server 109 can also transmit the request by email, phone, fax, mail, or other conventional means to the user computing device 107. The data server 109 may include computer software for formulating a request coupled to an output interface for transmitting the request to the user computing device 107. In the case of a request transmitted to the user computing device 107, a textual or voice messaging capabilities may be used to formulate a message. The message may solicit a touch-tone response which is detected and recorded by the data server 109, or a verbal response that is recorded by the data server 109. In some embodiments, if the user does not respond within a predetermined period of time or a response is incomplete or prompts further inquiry, a reminder or follow-up request may be provided to the user computing device 107. Once the correct and accurate data for missing field has been supplied by the user computing device 107, the data server 109 may remove any missing data tag from the user healthcare record, and update the user healthcare profile with information provided by the user in response to the request for missing data and store in the database 111. Additional calculations or assessments by the data server 109 may be performed based on information stored in the updated healthcare database record of the user stored in the database 111. Once the healthcare database record of the user is complete and accurate, the data server 109 may output the application or form corresponding to the user healthcare record to analytical engine of the system 100 for further processing. In some embodiments, the analytical engine or the data server 109 may apply one or more analytical models and/or algorithms on the healthcare record of the user stored in the database 111 to calculate healthcare reports and insights for the user. For example, the analytical models and/or algorithms executed by the analytical engine or the data server 109 may classify the information sources into categories that may be related to the type and origin of the healthcare information source, and then identify the relationships between collected healthcare information documents and generate corresponding insights such as clinical summary and health timeline of the user for a pre-defined interval of time.

Data Sources 103 may include any number of computing devices or machine-readable computer files providing the healthcare data service 101 with inbound data records in any number of data formats and data types. For example, a data source 103 may be a healthcare application server 115 that generates healthcare records (i.e., inbound records, EHR) according to the particular data model of the healthcare application (e.g., AllScripts®, EPIC®, MatrixCare®, AOD®, eHealthcare®). In some cases, the inbound records may be transmitted to a data server 109 of the healthcare data service 101 over any number of internal and external data networks 113. As another example of a data source 103, the inbound data records may be scanned from paper documents and transmitted to a data server 109 of the healthcare data service 101. As another example, a data source 103 may include a data repository 117 storing records according to any number of data formats (e.g., XML, JSON, RSS, SQL, text file, RSS) and/or data models (e.g., HL7, CCD, Delta, customized model), and may be transmitted to a data server 109 of the healthcare data service 101 or may be fetched by the data server 109 of the healthcare data service 101 based on a triggering condition (e.g., time-based periodic updates, real-time updates). In some cases, a data source 103 may include a financial institution, such as a health insurance provider, storing records of claim events, claim history, financial insured coverage, and the like, in a format of the financial institution. Additionally or alternatively, in some cases a data source 103 may include an end-user device 107 that may generate and transmit healthcare data to the healthcare data service 101. For example, in some instances, a data source 103 may include a wearable fitness tracker that may generate data records associated with fitness and motion activity of the consumer during periods of physical activity. This data may be provided from the wearable data source 103 to data server 109 and/or service database 111.

The data sources 103 may include any number of healthcare application servers 115 executing healthcare applications that generate electronic healthcare records having a prescribed data model associated with the particular healthcare application. In some instances, the data sources 103 may include a data repository 117 containing healthcare records stored in an electronic format on one or more servers, or other non-transitory machine-readable storage media. A data source 103 may be configured to provide inbound records to the healthcare data service 101 in any number of ways. For example, in some cases, a data repository 123 may be configured to periodically (e.g., daily) transmit via a data transfer protocol (e.g., FTP, SFTP).

A user device 107 may be any computing device comprising a processor configured to execute a healthcare application or a web browser application that accesses or receives data records from the healthcare data service 101. Non-limiting examples of the user device 107 may include a server computer, a workstation computer, a wearable device, a tablet device, and a mobile device (e.g., smartphone, PDA). In some instances, the user device 107 may execute a client-side healthcare application for manipulating or updating patient data stored in a service database 111. For example, a consumer may use a tablet device 131 configured to access the records that they have been granted access to, and having a predefined data model. The data server 109 may structure and output to the user device 107 portions of the requested patient data stored in the databases 111 according to the particular function requested by the user device 107.

In some embodiments, the user device 107 may be any computing and/or telecommunications device capable of performing the various tasks and processes described herein, such as accessing a webserver (not shown) and providing a GUI interface to a user to interact with a customer-centric website hosted on the webserver. In other words, the user device 107 may allow the user to interact with the data server 109 via the webserver. The user device 107 may execute an Internet browser or local application that access the webserver in order to issue requests or instructions to the data server 109 to access the system 100. The user device 107 may transmit credentials from user inputs to the webserver, from which the webserver may authenticate the user. One having skill in the art would appreciate that the user device 107 may comprise any number of input devices configured to receive any number of data inputs (e.g., mouse, keyboard, touchscreen, stylus), including various types of data inputs allowing for authentication, e.g., username, passwords, certificates, biometrics. One having skill in the art would also appreciate that the user device 107 may be any computing device comprising a processor and non-transitory machine-readable storage medium allowing the user device 107 to perform the various tasks and processes described herein.

As an example of the user device 107 operation, the user device 107 may execute an Internet browser that accesses the webserver hosting a website and/or healthcare application that allows for the user to access to the consolidated healthcare data and reports. Using the user device 107, a user may interact with various data published on the user-centric website and/or healthcare application. The user device 107 of the user may be used upload machine-readable computer files (e.g., PDF, DOC, XSL) containing healthcare and insurance information. The computer files may be stored into document records in the service database 111. The user device 107 may issue queries or instructions to the data server 109 via the webpages generated by the webserver, which then instruct the data server 109 to perform various tasks, such as retrieving or updating a file from the service database 111.

A webserver (not shown) may be any computing device hosting a website and/or healthcare application accessible to the user device 107 via the Internet. The webserver may be any computing device comprising a processor and non-transitory machine-readable storage capable of executing the various tasks and processes described herein. Non-limiting examples of such computing devices may include workstation computers, laptop computers, server computers, laptop computers, and the like. While the exemplary system 100 includes a single webserver, one having skill in the art would appreciate that in some embodiments the webserver may include any number of computing devices operating in a distributed computing environment.

The webserver may execute software applications configured to host the website (e.g., Apache®, Microsoft IIS®) and/or healthcare application, which may generate and serve various webpages to the user device 107. The website and/or healthcare application may be used to generate and access data stored on the service database 111. In some implementations, the webserver may be configured to require user authentication based upon a set of user authorization credentials (e.g., username, password, biometrics, cryptographic certificate). In such implementations, the webserver may access the service database 111 configured to store user credentials, which the webserver may be configured to reference in order to determine whether a set of entered credentials purportedly authenticating the user match an appropriate set of credentials that identify and authenticate the user. Similarly, in some implementations, the webserver may generate and serve webpages to the user device 107 based upon user membership specifics within the system 100. In such implementations, the user profile may be defined by data fields in user records stored in the service database 111, and authentication of the user may be conducted by the webserver by executing an access directory protocol. The webserver may then be instructed to generate webpage and/or healthcare application content, access or generate data stored in the service database 111, according to the user membership specifics defined by the user record in the service database 111.

Service databases 111 may be hosted on any server (such as a data server 109) and are capable of storing the user healthcare records and user healthcare profiles in plain format and/or encrypted version containing data fields that are associated with the communication channel and type of healthcare data-generating systems. The service databases 111 may further store user records that may comprise data fields describing users, e.g., user data, such as user credentials (e.g., username, passwords, biometrics, encryption certificates), user account data, user rules, or user permissions; document records that may comprise machine-readable computer files (e.g., word processing files), parsed portions of such computer files, or metadata associated with computer files; and application data that may include software instructions executed by the data server 109 or data used by the such applications executed by the data server 109. The service databases 111 may be in communication with a processor of the data server 109, where the processor is capable of executing the various commands of the system 100. In some embodiments, the service databases 111 may be part of the data server 109. In some embodiments, the service databases 111 may be a separate component in communication with the data server 109.

The service databases 111 may be in communication to the data server 109 via the network 113 and include a non-transitory machine-readable storage media capable of receiving, storing, updating healthcare records stored in the service databases 111. The service databases 111 may have a logical construct of data files that are stored in non-transitory machine-readable storage media, such as a hard disk or memory, controlled by software modules of a database program (for example, SQL), and a related database management system (DBMS) that executes the code modules (for example, SQL scripts) for various data queries and other management functions generated by the data server 109.

In some embodiments, a memory of the service databases 111 may be a non-volatile storage device for storing alert element data and instructions, to be used by a processor of the data server 109. The memory may be implemented with a magnetic disk drive, an optical disk drive, a solid-state device, or an attachment to a network storage. The memory may include one or more memory devices to facilitate storage and manipulation of program code, set of instructions, tasks, data, PDKs, and the like. Non-limiting examples of memory implementations may include, but are not limited to, a random access memory (RAM), a read only memory (ROM), a hard disk drive (HDD), a secure digital (SD) card, a magneto-resistive read/write memory, an optical read/write memory, a cache memory, or a magnetic read/write memory.

In some embodiments, a memory of the service databases 111 may be a temporary memory, meaning that a primary purpose of the memory is not long-term storage. Examples of the volatile memories may include dynamic random access memories (DRAM), static random access memories (SRAM), and other forms of volatile memories known in the art. In some embodiments, the memory may be configured to store larger amounts of information than volatile memory. The memory may further be configured for long-term storage of information. In some examples, the memory may include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

The healthcare data system 100 described herein, provide a number of advantages over the existing applications. The healthcare data system 100 provides an agnostic system that is able to implement interoperability of discrete medical records. In other words, the healthcare data system 100 can free health care information for each patient without the need to standardize the already existing industry practice. Instead of implementing standardization of data management, the healthcare data system 100 and process described herein can efficiently and accurately provide any one health care provider the ability to obtain a comprehensive and accurate record for each patient. The applications for such information are endless and can be applicable not only in the long term health care industry, where the problem of disparate data sources is most prevalent, but can also improve the information management in the acute health care practice. The healthcare data system 100 and methods described herein are able to make available a complete patient record to any device independent of the data system involved, including any desired mobile applications, allow the user to run any number of analytics, identify key performance indicators, and view the information in any number of different display modes.

Figure 2:
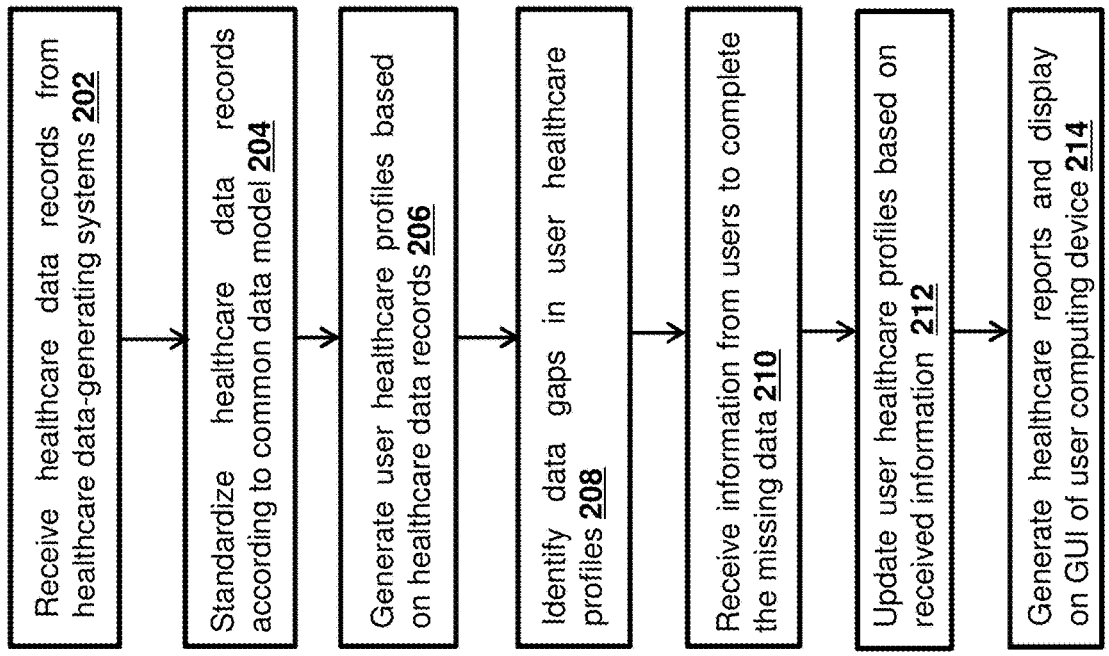
FIG. 2 shows execution of a method for generating healthcare reports and insights for a user, according to an exemplary embodiment.

FIG. 2 shows execution steps of generating healthcare reports and insights for a user, according to an exemplary method 200. The exemplary method 200 shown in FIG. 2 comprises execution steps 202, 204, 206, 208, 210, 212, and 214. However, it should be appreciated that other embodiments may comprise additional or alternative execution steps, or may omit one or more steps altogether. It should also be appreciated that other embodiments may perform certain execution steps in a different order; steps may also be performed simultaneously or near-simultaneously with one another. In addition, the exemplary method 200 of FIG. 2 is described as being executed by a single healthcare server computer in this exemplary embodiment. However, one having skill in the art will appreciate that, in some embodiments, steps may be executed by any number of computing devices operating in a distributed computing environment. In some cases, a computer executing one or more steps may be programmed to execute various other, unrelated features, where such computer does not need to be operating strictly as the healthcare server computer described herein.

In a first step 202, a healthcare server computer may receive a set of one or more healthcare data records containing a user identifier from one or more healthcare data-generating systems and data sources. The healthcare server may handle the healthcare data records based at least in part by configuring the one or more healthcare data-generating systems to subscribe to a data feed of healthcare information. In some embodiments, the data feed may be adapted to collect healthcare information in RSS format, OPML format, or other formats from the one or more healthcare data-generating systems such as fitness wearable devices, connected devices for weight tracking, connected devices for medical tracking, hospital data-generating systems, pharmacy data-generating systems, medical device, medical instrument, handheld medical device, a device associated with an operating room, a device configured to display an electronic medical record, a device configured to run a healthcare software application, and the like. In some embodiments, the healthcare data record may contain information selected from a group including, but not limited to, medical instruments, x-ray equipment, MRI equipment, other forms of medical imaging equipment, blood work data, genetic information, medical exam information, medical device information, information from emergency rooms, information from medical labs, diet information, exercise information, metabolic information, medical history information, age information, gender information, behavior information, race information, or information from other systems related to the healthcare and or medical field.

The one or more healthcare data-generating systems are typically configured to generate corresponding healthcare data record according to one or more data models associated with one or more formats and one or more data types. Each of the one or more healthcare data-generating systems may be configured to generate the corresponding healthcare data record according to a separate type of data model having a separate data type and a separate data format.

In a next step 204, the healthcare server computer standardize the set of one or more healthcare data records received from the one or more healthcare data-generating systems according to the one or more data models according to a common data model. The healthcare server computer may standardize the set of one or more healthcare data records having the one or more formats and the one or more data types by mapping the transformation of the one or more formats for all healthcare data records having all of the one or more data types to a single format and single data type. In some embodiments, the healthcare server computer may select the healthcare server computer based on recommendation of the user. In some embodiments, the healthcare server computer may select the healthcare server computer based on configuration of a user computing device.

Upon standardizing the set of one or more healthcare data records received from the one or more healthcare data-generating systems according to the common data model, the healthcare server computer may then store the standardized set of the one or more healthcare data records into the first database. The first database may store a plurality of healthcare data records associated with a plurality of user identifiers.

In a next step 206, the healthcare server computer generate, in a second database, a user healthcare profile associated with the user identifier based on the standardized set of the one or more healthcare data records stored in the first database. The user healthcare profile may include one or more data fields containing data from the standardized set of one or more healthcare data records associated with the user identifier in the first database. For instance, the user profile may include information such as heart rate, pulse rate, beat-to-beat heart variability, EKG or ECG, respiration rate, skin temperature, core body temperature, heat flow off the body, EMG, EEG, EOG, blood pressure, body fat, hydration level, activity level, oxygen consumption, glucose or blood sugar level, body position, pressure on muscles or bones, and UV radiation absorption. The second database is configured to store a plurality of user healthcare profiles associated with a plurality of user identifiers.

In some embodiments, upon the creation of the user healthcare profile, the healthcare server computer may determine one or more action items associated with the data in each of the one or more data fields in the user healthcare profile. Each action item may be programmed and/or scheduled to be performed within a predetermined period of time. The healthcare server computer may then determine the predetermined period of time during which each of the one or more action items has to be executed by the user. Upon the determination of the one or more action items to be executed by the user within the predetermined period of time, the healthcare server computer is then configured to trigger a monitoring window for a time period to measure the time period from the determination of the one or more action items until the predetermined period of time elapses for each of the one or more action items. During the monitoring window, the healthcare server computer periodically checks whether a record of execution of each of the one or more action items by the user is either available from the one or more healthcare data-generating systems or has been received in an internal database from the one or more healthcare data-generating systems/user. In one example case, the healthcare server computer on processing the data in each of the one or more data fields in the user healthcare profile may identify a record indicating a referral for a user to visit a doctor on a certain date and time. For instance, a healthcare server computer may determine on Jan. 20, 2016 that a record in the user healthcare profile indicates that a doctor A on Jan. 15, 2016 referred the user to visit a doctor B, which is most likely to occur by Mar. 15, 2016. Then the healthcare server computer may trigger a monitoring window and/or a timer to track the visit of the user to the doctor B. The healthcare server computer may monitor the visit of the user to doctor B until Mar. 15, 2016. On Mar. 16, 2016, the healthcare server computer may check an internal database to determine whether any record of user visit to the doctor B prior to Mar. 15, 2016 has been received from the one or more healthcare data-generating systems. In some instances, the healthcare server computer upon determining that no record of the user visit to the doctor B prior to Mar. 15, 2016 is available in the internal database, which may be represented as a gap in the record, so the healthcare server computer may generate a request corresponding to a confirmation response for verification of the user visit to the doctor B prior to Mar. 15, 2016. The healthcare server computer then transmits the request to the one or more healthcare data-generating systems. The one or more healthcare data-generating systems upon receiving the request may transmit a message to the healthcare server computer regarding whether there exists a record of the user visit to the doctor B prior to Mar. 15, 2016 or not.

In a next step 208, the healthcare server computer identify one or more data gaps corresponding to missing data in the user healthcare profile associated with a user based on examination of data in the one or more data fields of the user healthcare profile. In some embodiments, the examination of the data by the healthcare server computer may correspond to determination by the healthcare server computer whether there is any record of execution of the one or more action items by the user within the predetermined period of time. The healthcare server computer may locate the record of the execution of the one or more action items in the internal database or request the record from the one or more healthcare data-generating systems. In some embodiments, the examination of data in the one or more data fields of the user healthcare profile may include determining by the computer a link between user actions and sources of data contained in the one or more data fields. In some embodiments, the examination of data in the one or more data fields of the user healthcare profile may include determining by the computer a link between all the data contained in each of the one or more data fields. For example, the healthcare server computer on processing the healthcare data records in the user healthcare profile may identify a data gap where the healthcare server computer may determine that the user got a referral from a primary care doctor to see an orthopedics doctor but the healthcare server computer did not identify any visit by the user to the orthopedics doctor on processing of the user healthcare data records. In such a case, the healthcare server computer may generate a flag for potential gap or missing information regarding potential orthopedics doctor visit by the user. In another example case, the healthcare server computer on processing the healthcare data records in the user healthcare profile may identify a data gap when a user is taking a medication for a disease such as high blood pressure, but the healthcare server computer did not identify a doctor's visit by the user where the user actually got diagnosed with high blood pressure on processing of the user healthcare data records. In such a case, the healthcare server computer may generate a flag for potential gap or missing information regarding potential doctor visit by the user. The healthcare server computer stores the potential gap or missing information in the database and is used by the healthcare server computer to determine what follow up actions need to be taken.

In a next step 210, the healthcare server computer upon identifying the one or more data gaps in the user healthcare profile associated with the user because there is no record of execution of the one or more action items within the predetermined period of time, may then generate a request for a user to execute the one or more action items. The healthcare server computer may provide the user with information corresponding to the one or more action items within the request. The information may include a new deadline date and time schedule to execute the one or more action items. In some instances, the healthcare server computer may communicate (through wired or wireless communication platform) with the one or more healthcare data-generating systems to determine the new deadline date and time schedule for the user to execute the one or more action items.

In some embodiments, the healthcare server computer upon identifying the one or more data gaps in the user healthcare profile associated with the user may generate a request to complete the data gaps in the healthcare database record. The healthcare server computer may transmit the request to an user computing device operated by the user in order to provide information corresponding to the one or more data gaps in the user healthcare profile. In some embodiments, the healthcare server computer may request the user computing device for additional information by populating fields marked as incomplete or missing in a webpage displayed on the user computing device as part of the request. In some embodiments, if the user does not respond within a predetermined period of time or a response is incomplete or prompts further inquiry, a reminder or follow-up request may be provided to the user computing device by the healthcare server computer.

In a next step 212, the healthcare server computer update the user healthcare profile in the second database upon receiving the information corresponding to the one or more data gaps from the user computing device. In some embodiments, additional calculations or assessments by the healthcare server computer may be performed based on information stored in the updated healthcare database record of the user stored in the database. Once the healthcare database record of the user is complete, the healthcare server computer may output process the data within the healthcare database record to generate healthcare reports and insights.

In a next step 214, the healthcare server computer display the one or more healthcare reports and insights based on evaluation of the data in the one or more data fields of the user healthcare profile on a graphical user interface of the user computing device. The one or more healthcare reports and insights may include ovulation report based on analysis of skin temperature, core temperature, and oxygen consumption obtained from the user healthcare profile; sleep onset/wake report based on analysis of heart rate, pulse rate, and respiration data obtained from the user healthcare profile; calories burned report based on analysis of heart rate, pulse rate, respiration rate, heat flow, activity, and oxygen consumption data obtained from the user healthcare profile; metabolic rate report based on analysis of heart rate, pulse rate, respiration rate, heat flow, activity, and oxygen consumption data obtained from the user healthcare profile; and activity level report based on heart rate, pulse rate, respiration rate, heat flow; stress level report based on analysis of heart rate, pulse rate, respiration rate, skin temperature, heat flow, galvanic skin; and relaxation level report based on EKG, beat-to-beat variability, heart rate, and pulse rate data obtained from the user healthcare profile.

Figure 3A:
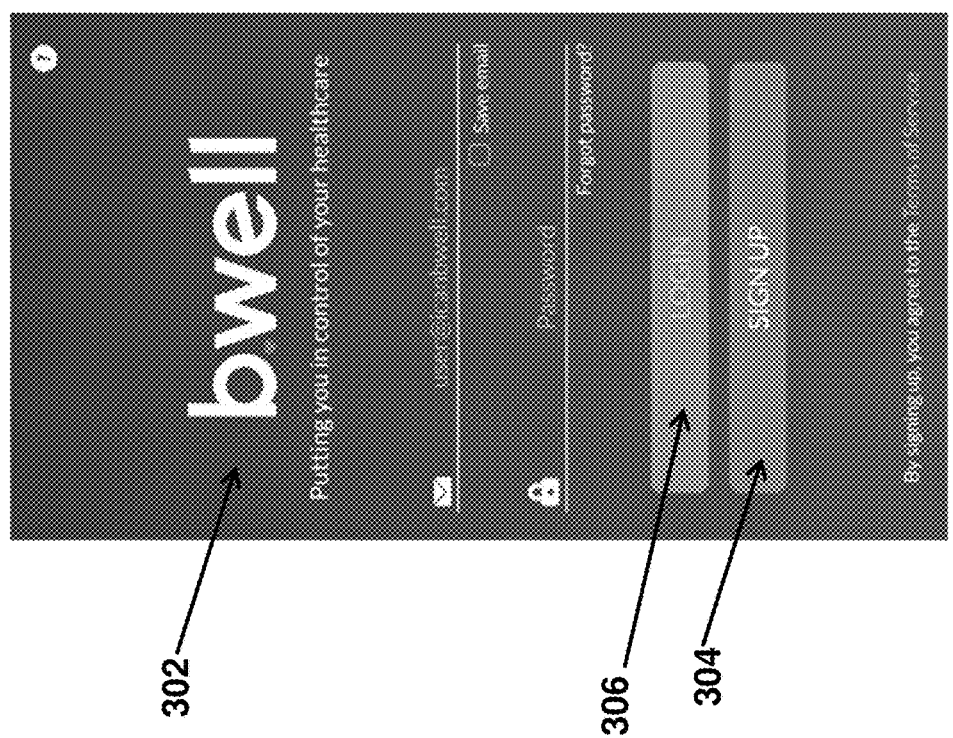
FIG. 3A illustrates a graphical user interface showing a webpage executed on a computing device of a user, according to an exemplary embodiment.

FIG. 3A illustrates a graphical user interface 300 showing a webpage 302 executed on a computing device of a user, according to an exemplary embodiment. In some embodiments, the computing device may be any portable or non-portable device, such as a desktop computer, a laptop computer, a tablet computer, a smart phone, a smart watch, a gaming console, a personal digital assistant, or the like. The computing device may include a processor/microcontroller and/or any other electronic component that performs one or more operations according to one or more programming instructions. The computing device may be capable of communicating with a system server through a communications network using wired or wireless communication capabilities.

A healthcare management application may be installed on the computing device of the user or may be configured to display on a website of a healthcare company. In some embodiments, a healthcare management application is installed on a computing device of an employer, a provider, and/or a payer. For example, a healthcare company may generate the healthcare application as a widget configured to communicate with different users, employers, providers, and payers and the widget may be displayed on the website of the healthcare company. A computing device may have access to one or more databases or pre-stored web-based interfaces, such as webpages, comprising a number of preconfigured sub-interfaces, or containers, that are dynamically populated (e.g., widget box). For example, healthcare application webpages may contain code, such as HTML or PHP, presenting a website of any number of webpages having a common look-and-feel. One or more outputs or results may display webpages 302 that may contain additional code for containers, where the container code displays the healthcare application widget. A user may access a webpage 302 and interact with the computing device via the healthcare application. In some implementations, the computing device may be configured to require user authentication based upon a set of user authorization credentials (e.g., username, password, biometrics, cryptographic certificate) to provide access to the healthcare application on the computing device. For example, the computing device may access a database configured to store the user credentials, which a webserver may be configured to reference in order to determine whether a set of entered credentials purportedly authenticating the user match an appropriate set of credentials that identify and authenticate the user. Similarly, in some implementations, the webserver may generate and serve applications/webpages associated to the healthcare application to the computing device based upon a user membership account. In some embodiments, the webserver may generate and serve applications/webpages associated to the healthcare application (such as the webpage 302) to the computing device based upon the user membership. In such implementations, the user membership may be defined by data fields in the user records stored in the database, and authentication of the user and the user membership may be conducted by the webserver by executing an access directory protocol.

During operation, a user may access the webpage 302 by any common access method, e.g., keying in a URL, selecting from search results, etc., and submit user credentials to access the healthcare application. Upon the webserver authenticating the user using credentials that identify the user as a valid member of the healthcare application company, the user is presented the healthcare application. For instance, the healthcare application may be a description window that may provide information regarding creating an account (via SIGN UP button) 304. If the user already has an account, the user may click "LOGIN" button 306 on the healthcare application to access their account by providing the email address and the password information.

FIG. 3B1 illustrates a graphical user interface 308 showing a webpage executed on a computing device of a user, according to an exemplary embodiment. A healthcare management application may be installed on the computing device of the user. In some embodiments, a healthcare management application is installed on a computing device of an employer, provider, and/or payer. Upon registering an account with a healthcare management application, the user may select a tab 310 to connect one or more wearable devices that track sleep, fitness, and nutrition of the user with a healthcare management application. Upon the synchronization of the one or more wearable devices with the healthcare management application, a server of the healthcare management application may receive health data 312 such as a number of steps of the user in a given day, a number of calories burned of the user in a given day, blood pressure of the user, heart rate of the user, among other information.

In some embodiments, the one or more wearable devices may include an earpiece, gown, wristband, or other such structures for positioning one or more modules configured to communicate in a vicinity of a user who wears the structure(s). Other embodiments may be configured to communicate with a stationary or other module and/or to include one or more sensors for detecting status indicia relating to the user. The one or more wearable devices may preferably be worn by an individual user on his or her body. The one or more wearable devices may be adapted to generate signals in response to physiological characteristics of the user and a microprocessor. In some cases, the one or more wearable devices may generate data indicative of various physiological parameters of the user, such as the user's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation absorption. In certain cases, the data indicative of the various physiological parameters of the user is the signal or signals themselves generated by the one or more wearable devices and in certain other cases the data is calculated by the microprocessor based on the signal or signals generated by the one or more wearable devices.

In some embodiments, a server of the healthcare management application may be programmed to summarize and analyze the data received from the one or more wearable devices. For example, the server can be programmed to calculate an average, minimum or maximum rate such as heart rate or respiration rate over a defined period of time.

In some embodiments, the one or more wearable devices may include one or more sensor devices that may generate data indicative of various contextual parameters relating to the environment surrounding the user. For example, the sensor device can generate data indicative of the air quality, sound level/quality, light quality or ambient temperature near the user. The sensor device may include a processor for generating signals in response to contextual characteristics relating to the environment surrounding the user and the signals may be used to generate the healthcare data record of the user.

FIG. 3B2 illustrates a graphical user interface 313 showing a webpage executed on a computing device of a user, according to an exemplary embodiment. A healthcare management application may be installed on the computing device of the user. In some embodiments, a healthcare management application is installed on a computing device of an employer, provider, and/or payer. Upon registering an account with a healthcare management application, the user may provide clinical record authorization. For instance, the user may authorize a processor of the healthcare management application to connect to one or more clinics and one or more physicians of the user and obtain the records associated with the user.

Figure 3C:
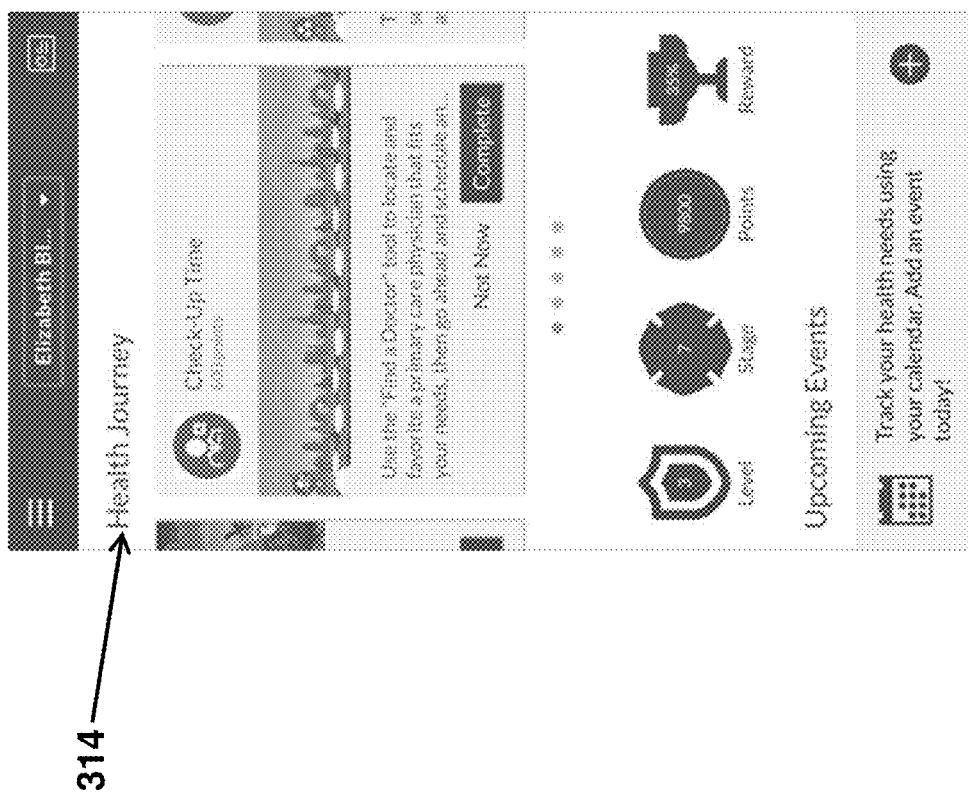
FIG. 3C illustrates a graphical user interface showing a webpage executed on a computing device of a user, according to an exemplary embodiment.

FIG. 3C illustrates a graphical user interface 314 showing a webpage executed on a computing device of a user, according to an exemplary embodiment. A healthcare management application may be installed on the computing device of the user. In some embodiments, a healthcare management application is installed on a computing device of an employer, provider, and/or payer. The healthcare management application account of the user displayed on the graphical user interface 314 may display a healthcare profile of the user that may include information such as health journey of the user, one or more connected sources to the healthcare management application, user health records (My Health), and financial data of the user collected from various data sources.

Figure 3D:
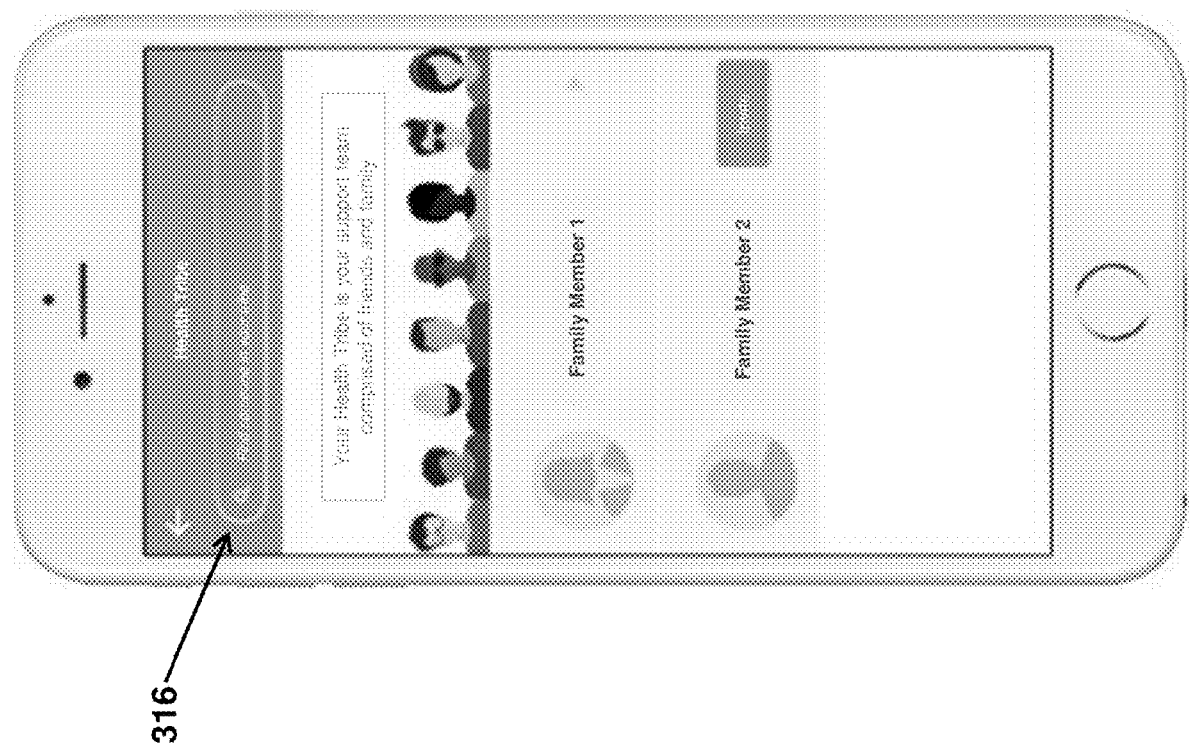
FIG. 3D illustrates a graphical user interface showing a webpage executed on a computing device of a user, according to an exemplary embodiment.

FIG. 3D illustrates a graphical user interface 316 showing a webpage executed on a computing device of a user, according to an exemplary embodiment. A healthcare management application may be installed on the computing device of the user. In some embodiments, a healthcare management application is installed on a computing device of an employer, provider, and/or payer. The healthcare management application account of the user displayed on the graphical user interface 316 may provide an option to the user to add one or more family members healthcare data.

Figure 3E:
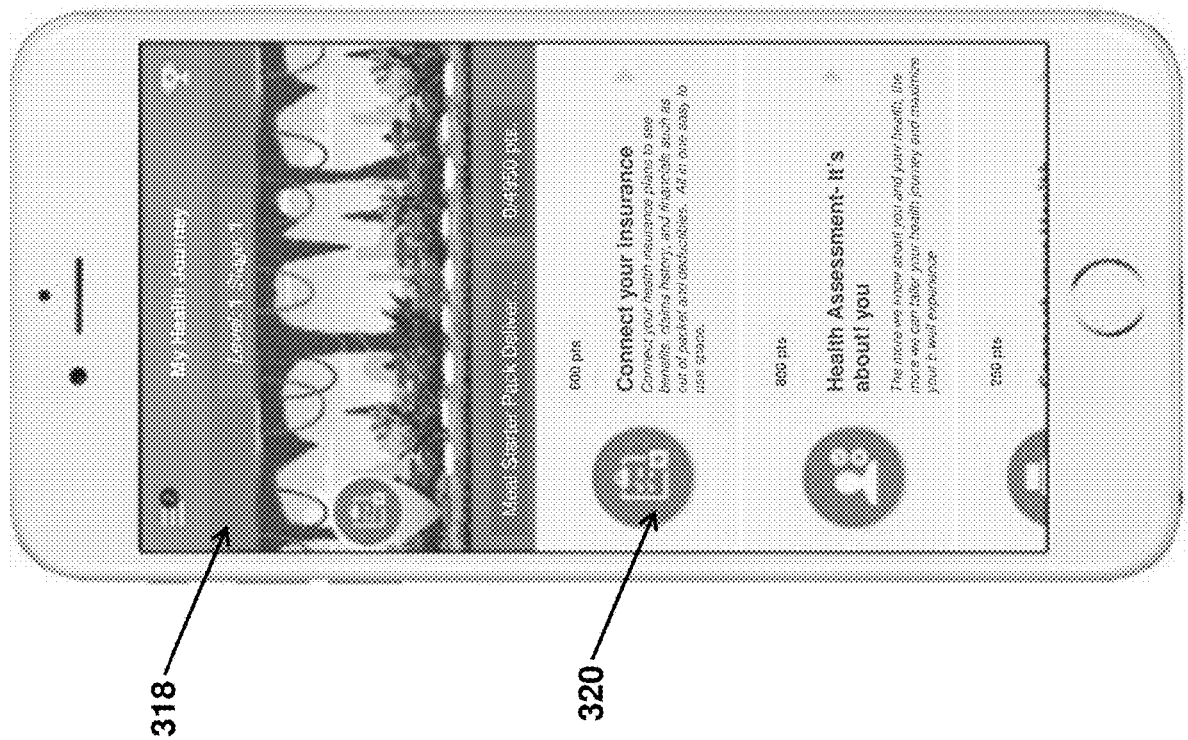
FIG. 3E illustrates a graphical user interface showing a webpage executed on a computing device of a user, according to an exemplary embodiment.
Figure 3F:
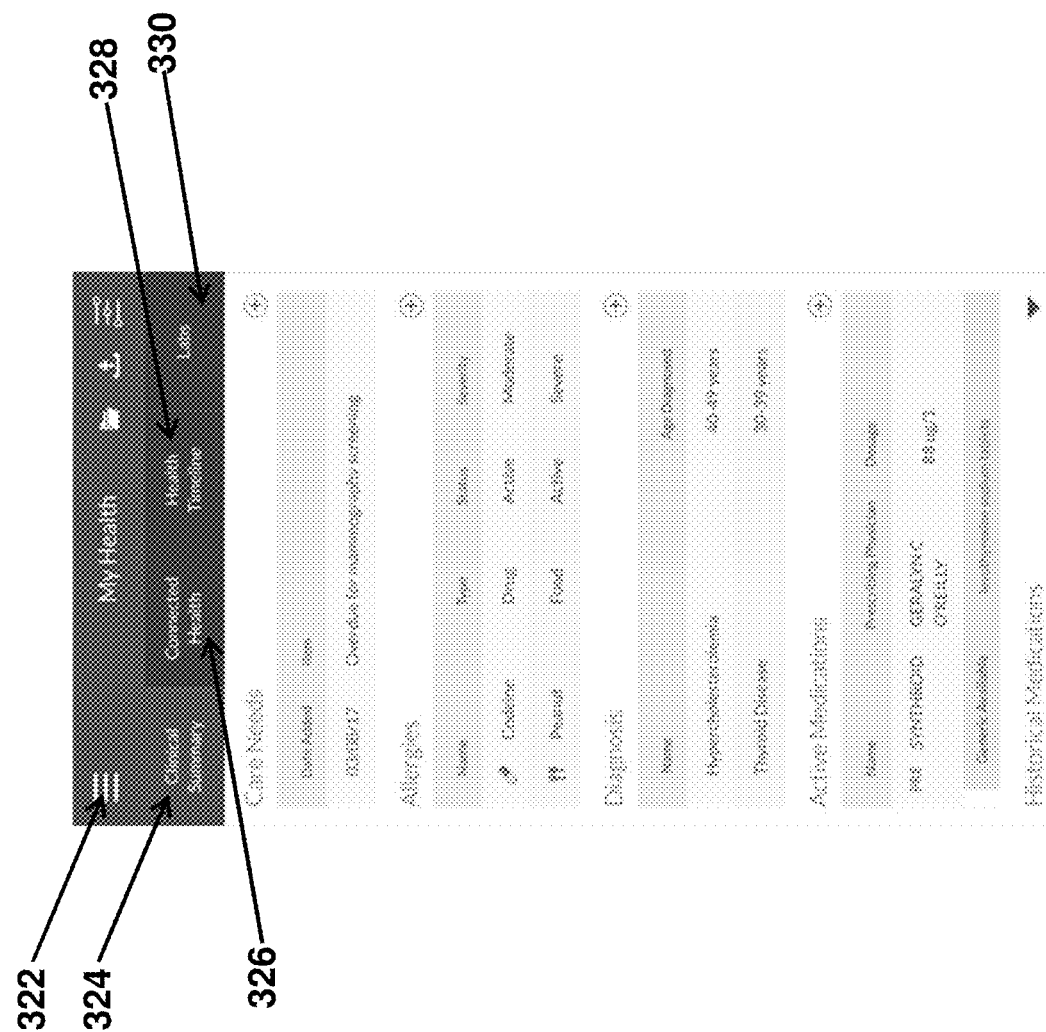
FIG. 3F illustrates a graphical user interface showing a webpage executed on a computing device of a user, according to an exemplary embodiment.
Figure 3G:
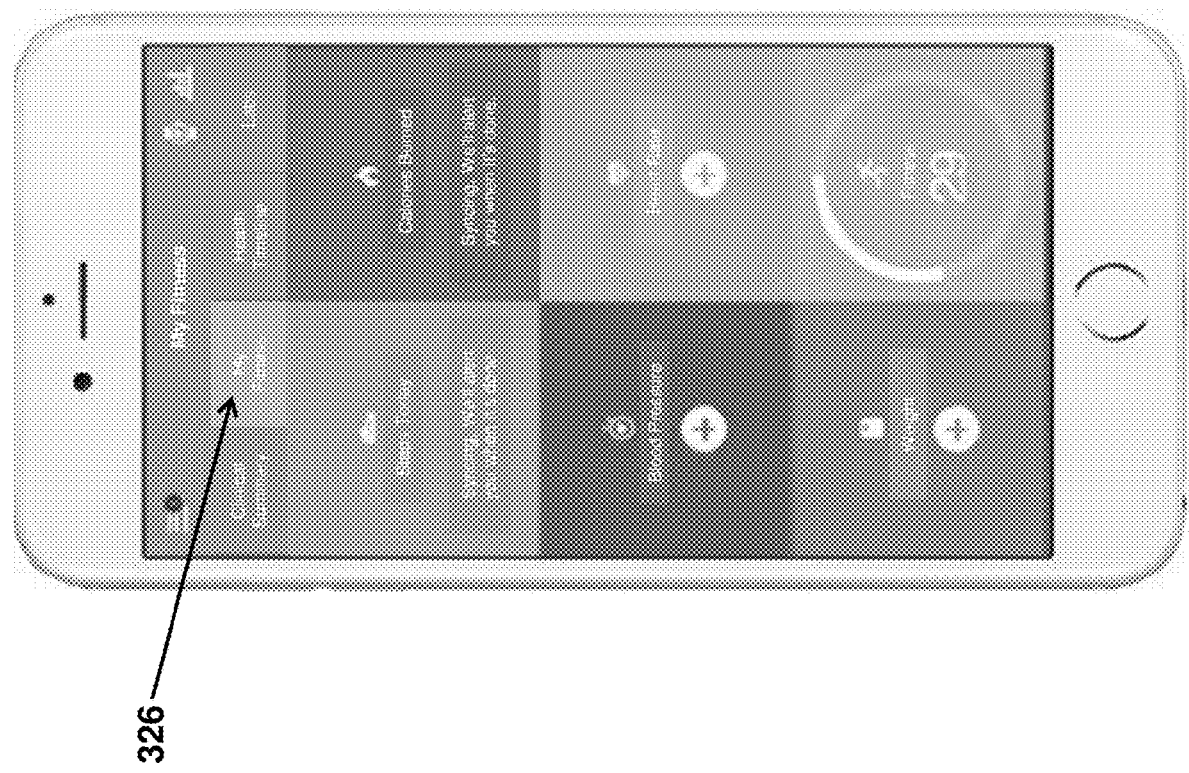
FIG. 3G illustrates a graphical user interface showing a webpage executed on a computing device of a user, according to an exemplary embodiment.
Figure 3H:
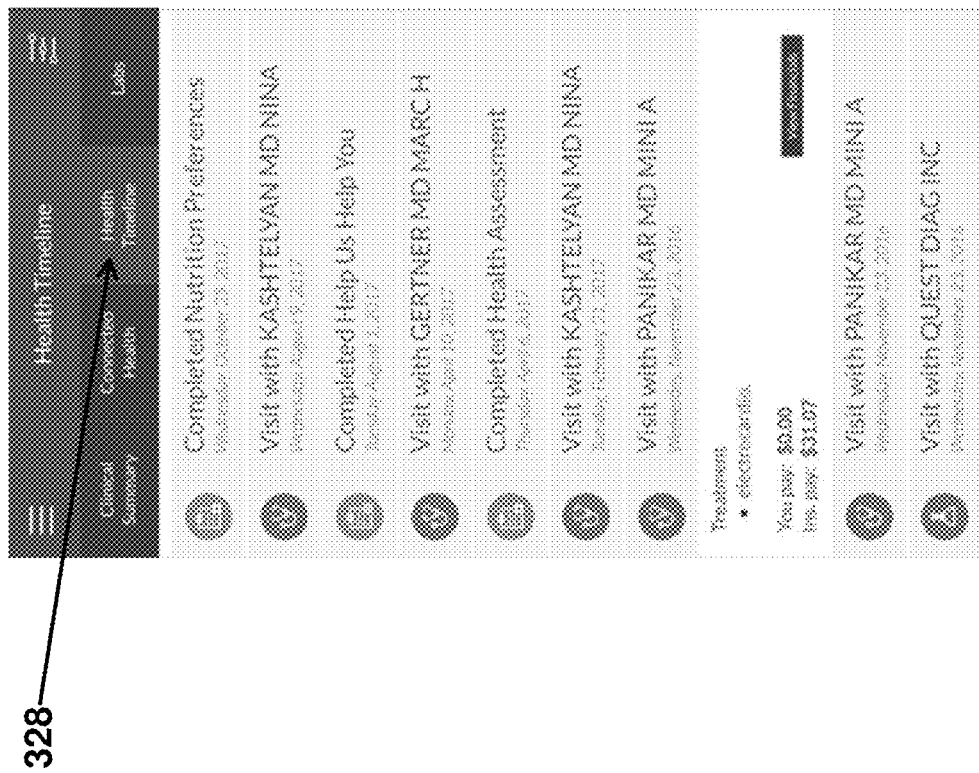
FIG. 3H illustrates a graphical user interface showing a webpage executed on a computing device of a user, according to an exemplary embodiment.
Figure 31:
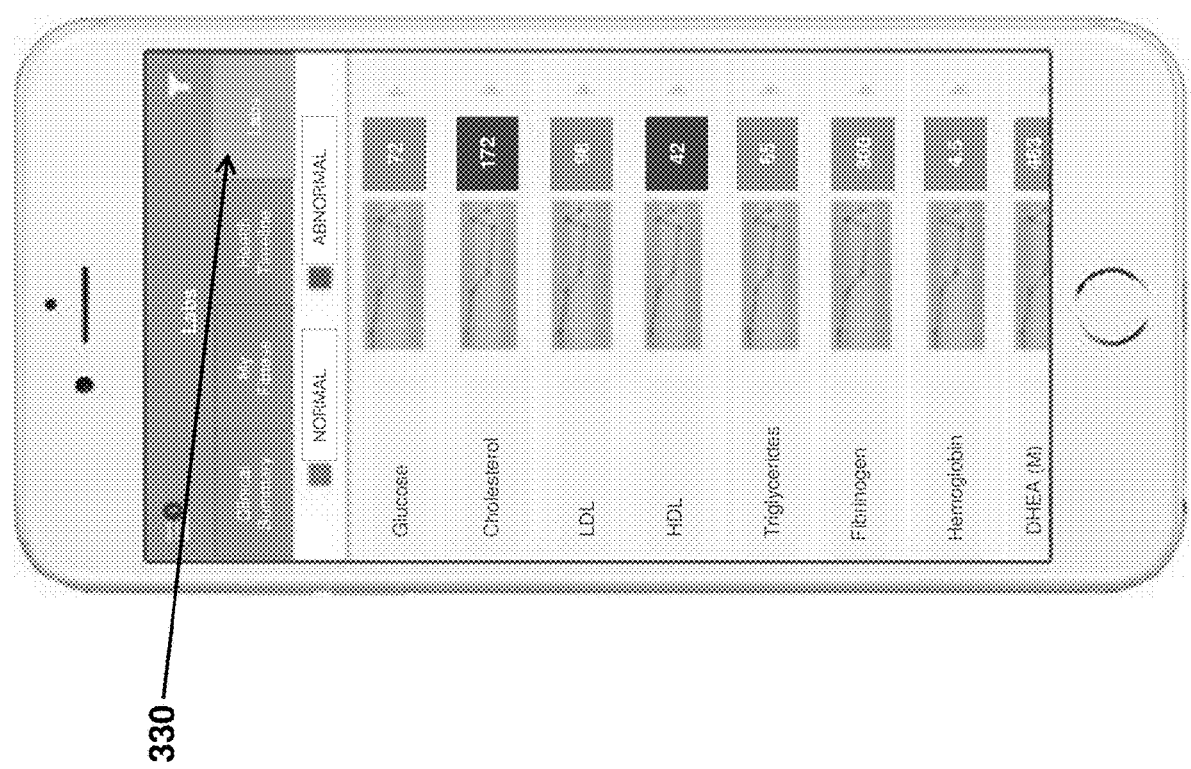

FIG. 3E illustrates a graphical user interface 318 showing a webpage executed on a computing device of a user, according to an exemplary embodiment. A healthcare management application may be installed on the computing device of the user. In some embodiments, a healthcare management application is installed on a computing device of an employer, provider, and/or payer. Upon registering an account with a healthcare management application, the user may select a tab 320 to connect with one or more insurance plans that track of benefits, claims history, and financial such as out of pocket and deductibles. Upon the synchronization of the one or more insurance plans with the healthcare management application, the server of the healthcare management application may receive insurance data such as benefits information and claim information. In some embodiments, a server of the healthcare management application may be programmed to summarize and analyze the data received from the one or more insurance plans.

FIG. 3F, FIG. 3G, FIG. 3H, and FIG. 3I illustrates a graphical user interface 322 showing a webpage executed on a computing device of a user, according to an exemplary embodiment. A healthcare management application may be installed on the computing device of the user. In some embodiments, a healthcare management application is installed on a computing device of an employer, provider, and/or payer. The healthcare management application account of the user displayed on the graphical user interface 322 may provide one or more healthcare reports generated based on analysis of healthcare data of the user collected from multiple data sources and data generating systems. The one or more healthcare reports may include a tab for clinical summary 324, a tab for my fitness 326, a tab for health timeline 328, and a tab for labs 330. The user upon selecting the tab for clinical summary 324 may display information such as care needs, allergies, diagnosis, medications, and surgeries. The user upon selecting the tab for my fitness 326 may display information such as number of steps taken by the user, number of calories burned by the user, blood pressure of the user, heart rate of the user, and weight of the user. The user upon selecting the tab for the health timeline 328 may be able to view completed health assessment. The user upon selecting the tab for labs 330 may be able to view lab results such as for glucose, cholesterol, etc.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A computer-implemented method comprising:
receiving, by a computer, a set of one or more healthcare data records containing a user identifier from one or more healthcare data-generating systems configured to generate a corresponding healthcare data record, wherein the one or more healthcare data-generating systems are configured to generate the corresponding healthcare data record according to one or more data models associated with one or more formats and one or more data types;
standardizing, by the computer, the set of one or more healthcare data records received from the one or more healthcare data-generating systems according to a common data model comprising mappings specifying transformations from the one or more formats for all healthcare data records having all of the one or more data types to a single format and single data type;
storing, by the computer, the standardized set of one or more healthcare data records into a first database configured to store a plurality of healthcare data records associated with a plurality of user identifiers;
generating, by the computer, in a second database, a user healthcare profile of a user associated with the user identifier, the user healthcare profile comprising one or more data fields containing data from the standardized set of one or more healthcare data records associated with the user identifier in the first database, wherein the second database is configured to store a plurality of user healthcare profiles associated with a plurality of user identifiers, and wherein each user healthcare profile contains one or more action items associated with data in each of the one or more data fields;

determining, by the computer, that the user healthcare profile contains a first record of a first action item that requires entry of a second record indicating that a second action item has been performed, wherein the second record of the second action item is programmed to require a record of execution within a predetermined period of time;

determining, by the computer, that the predetermined period of time has elapsed;

responsive to determining that the predetermined period of time has elapsed, determining whether a record of execution of the second action item is available from the one or more healthcare data-generating systems after the predetermined period of time elapses, wherein the computer is configured to trigger a monitoring window for a time period from determination of the first action item until the predetermined period of time elapses to determine the execution of the second action item;

identifying, by the computer, one or more data gaps corresponding to missing data in the user healthcare profile based on a link between the first data record for the first action item and the second data record for the second action item and when the second record does not contain the record of execution of the second action item within the predetermined period of time from the first action item; and upon the computer identifying the one or more data gaps in the user healthcare profile responsive to determining that there is no link between the first and second data records and there is no record of execution of the second action item within the predetermined period of time:

transmitting, by the computer, a web link to a secure webpage comprising a request to a user computing device operated by the user, wherein the request comprises an instruction to populate missing information in the one or more data gaps representing execution of the second action item in the user healthcare profile and to execute the second action item;

updating, by the computer, the user healthcare profile in the second database upon receiving the information corresponding to the one or more data gaps representing execution of the second action item from the user computing device; and displaying, by the computer, one or more healthcare reports based on evaluation of the data in the one or more data fields of the user healthcare profile on a graphical user interface of the user computing device.

2. The computer-implemented method according to claim 1, wherein the common data model is selected by the user.

3. The computer-implemented method according to claim 1, wherein the common data model is selected by the computer based on a configuration of the user computing device.

4. The computer-implemented method according to claim 1, wherein the healthcare data record of the set of one or more healthcare data records comprises machine-readable code containing data fields describing detected user actions and sources of data associated with the user identifier.

5. The computer-implemented method according to claim 1, wherein the one or more healthcare data-generating systems comprises fitness wearable devices, connected devices for weight tracking, connected devices for medical tracking, hospital data-generating systems, and pharmacy data-generating systems.

6. The computer-implemented method according to claim 1, further comprising formatting, by the computer, the set of one or more healthcare data records received from the one or more healthcare data-generating systems.

7. The computer-implemented method according to claim 1, further comprising filtering, by the computer, the plurality of healthcare data records associated with the plurality of user identifiers for each user to generate each of the plurality of user healthcare profiles comprising data associated with each of the plurality of user identifiers.

8. The computer-implemented method according to claim 1, further comprising determining, by the computer, whether the data contained in the one or more data fields of the user healthcare profile comprises a partial amount of information based on identification of relationships of the data in the one or more data fields of the user healthcare profile with respect to each other.

9. The computer-implemented method according to claim 1, further comprising generating, by the computer, the one or more healthcare reports based on execution of one or more analytical algorithm models on the data in the one or more data fields of the user healthcare profile.

10. The computer-implemented method according to claim 1, further comprising:

generating, by the computer, one or more alerts based on application of one or more rules on data associated with the one or more healthcare reports; and transmitting, by the computer, the one or more alerts on the user computing device at one or more pre-defined time-intervals.

11. A system comprising:

a first database configured to store healthcare data records;

a second database configured to store user healthcare profiles; and a computer configured to:

receive a set of one or more healthcare data records containing a user identifier from one or more healthcare data-generating systems configured to generate a corresponding healthcare data record, wherein the one or more healthcare data-generating systems are configured to generate the corresponding healthcare data record according to one or more data models associated with one or more formats and one or more data types;

standardize the set of one or more healthcare data records received from the one or more healthcare data-generating systems according to a common data model comprising mappings specifying transformations from the one or more formats for all healthcare data records having all of the one or more data types to a single format and single data type;

store the standardized set of one or more healthcare data records into the first database configured to store a plurality of healthcare data records associated with a plurality of user identifiers;

generate in a second database, a user healthcare profile of a user associated with the user identifier, the user healthcare profile comprising one or more data fields containing data from the standardized set of one or more healthcare data records associated with the user identifier in the first database, wherein the second database is configured to store a plurality of user healthcare profiles associated with a plurality of user identifiers, and wherein each user healthcare profile contains one or more action items associated with data in each of the one or more data fields;

determine that the user healthcare profile contains a first record of a first action item that requires entry of a second record indicating that a second action item has been performed, wherein the second record of the second action item is programmed to require a record of execution within a predetermined period of time;

determine that the predetermined period of time has elapsed;

responsive to determining that the predetermined period of time has elapsed, determine whether a record of execution of the second action item is available from the one or more healthcare data-generating systems after the predetermined period of time elapses, wherein the computer is configured to trigger a monitoring window for a time period from determination of the first action item until the predetermined period of time elapses to determine the execution of the second action item;

identify one or more data gaps corresponding to missing data in the user healthcare profile based on a link between the first data record for the first action item and the second data record for the second action item and when the second record does not contain the record of execution of the second action item within the predetermined period of time from the first action item; and upon the computer identifying the one or more data gaps in the user healthcare profile responsive to determining there is no link between the first and second data records and there is no record of execution of the second action item within the predetermined period of time:

transmit a web link to a secure webpage comprising a request to a user computing device operated by the user, wherein the request comprises an instruction to populate missing information in the one or more data gaps representing execution of the second action item in the user healthcare profile and to execute the second action item;

update the user healthcare profile in the second database upon receiving the information corresponding to the one or more data gaps representing execution of the second action item from the user computing device; and display one or more healthcare reports based on evaluation of the data in the one or more data fields of the user healthcare profile on a graphical user interface of the user computing device.

12. The system according to claim 11, wherein the healthcare data record of the set of one or more healthcare data records comprises machine-readable code containing data fields describing detected user actions and sources of data associated with the user identifier.

13. The system according to claim 11, wherein the one or more healthcare data generating systems comprises fitness wearable devices, connected devices for weight tracking, connected devices for medical tracking, hospital data-generating systems, and pharmacy data generating systems.

14. The system according to claim 11, wherein the computer is further configured to determine whether the data contained in the one or more data fields of the user healthcare profile comprises a partial amount of information based on identification of relationships of the data in the one or more data fields of the user healthcare profile with respect to each other.

15. The system according to claim 11, wherein the computer is further configured to:

generate one or more alerts based on application of one or more rules on data associated with the one or more healthcare reports; and transmit the one or more alerts on the user computing device at one or more pre-defined time intervals.

16. A computer-implemented method comprising:

receiving, by a computer, a set of one or more healthcare data records containing a user identifier from one or more healthcare data-generating systems configured to generate a corresponding healthcare data record, wherein the one or more healthcare data-generating systems are configured to generate the corresponding healthcare data record according to one or more data models associated with one or more formats and one or more data types;

standardizing, by the computer, the set of one or more healthcare data records received from the one or more healthcare data-generating systems according to a common data model comprising mappings specifying transformations from the one or more formats for all healthcare data records having all of the one or more data types to a single format and single data type;

storing, by the computer, the standardized set of one or more healthcare data records into a first database configured to store a plurality of healthcare data records associated with a plurality of user identifiers;

generating, by the computer, in a second database, a user healthcare profile associated with the user identifier, the user healthcare profile comprising one or more data fields containing data from the standardized set of one or more healthcare data records associated with the user identifier in the first database, wherein the second database is configured to store a plurality of user healthcare profiles associated with a plurality of user identifiers, and wherein each user healthcare profile contains one or more action items associated with data in each of the one or more data fields;

identifying, by the computer, one or more data gaps corresponding to missing data in the user healthcare profile associated with a user based on a link between data records contained in each of the one or more data fields and wherein a linked data record does not contain a record of execution of an action item; and upon the computer identifying the one or more data gaps in the user healthcare profile associated with the user responsive to determining there is no link between the data records contained in each of the one or more data fields:

transmitting, by the computer, a web link to a secure webpage comprising a request to populate missing information in the one or more data gaps representing executing of the action item in the user healthcare profile to a user computing device operated by the user;

updating, by the computer, the user healthcare profile in the second database upon receiving the information corresponding to the one or more data gaps representing executing of the action item from the user computing device; and displaying, by the computer, one or more healthcare reports based on evaluation of the data in the one or more data fields of the user healthcare profile on a graphical user interface of the user computing device.

17. The computer-implemented method according to claim 16, wherein the common data model is selected by the user.

18. The computer-implemented method according to claim 16, wherein the common data model is selected by the computer based on a configuration of the user computing device.

19. The computer-implemented method according to claim 16, wherein the one or more healthcare data-generating systems comprises fitness wearable devices, connected devices for weight tracking, connected devices for medical tracking, hospital data-generating systems, and pharmacy data-generating systems.

20. The computer-implemented method according to claim 16, further comprising generating, by the computer, the one or more healthcare reports based on execution of one or more analytical algorithm models on the data in the one or more data fields of the user healthcare profile.

\* \* \* \* \*